United States Patent [19]

Estreicher et al.

[11] Patent Number: 4,486,427

[45] Date of Patent: Dec. 4, 1984

[54] INSECTICIDAL N-SUBSTITUTED-2-(HALONITROMETHYLENE) TETRAHYDRO-2H-1,3-THIAZINES

[75] Inventors: Herbert Estreicher; Samuel B. Soloway, both of Modesto, Calif.

[73] Assignee: Shell Oil Company, Houston, Tex.

[21] Appl. No.: 476,008

[22] Filed: Mar. 17, 1983

[51] Int. Cl.³ .................... A01N 43/86; C07D 279/06
[52] U.S. Cl. ....................................... 424/246; 544/54
[58] Field of Search ........................... 544/54; 424/246

[56] References Cited

U.S. PATENT DOCUMENTS

| | | | |
|---|---|---|---|
| 3,933,809 | 1/1976 | Powell | 544/54 |
| 3,985,736 | 10/1976 | Powell et al. | 544/54 |
| 3,993,648 | 11/1976 | Powell | 260/243 R |
| 4,225,603 | 9/1980 | Tieman | 544/54 |

*Primary Examiner*—John M. Ford

[57] ABSTRACT

Insecticidal 2-(halonitromethylene)-tetrahydro-2H-1,3-thiazines substituted on the nitrogen atom of the ring by a sulfonyl moiety.

8 Claims, No Drawings

INSECTICIDAL N-SUBSTITUTED-2-(HALONITROMETHYLENE) TETRAHYDRO-2H-1,3-THIAZINES

DESCRIPTION OF THE INVENTION

It has been found that useful insecticidal activity is possessed by compounds of the formula:

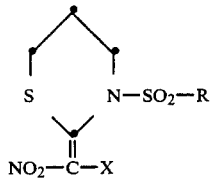
(I)

wherein X is bromine, chlorine or fluorine and R contains up to twenty carbon atoms and is optionally substituted alkyl.

The alkyl moiety may be either straight-chain or branched-chain in configuration. Suitable substituents include one or more halogen (bromine, chlorine, fluorine, iodine) atoms, alkoxy, alkylcarbonyl, alkoxycarbonyl, alkylcarbonyloxy, optionally substituted phenyl and phenoxy, and alkenyl. Suitable substituents on the phenyl and phenoxy moieties include halogen and haloalkyl (bromine, chlorine, fluorine), cyano, nitro, amino, mono- and di-alkylamino, alkyl, alkoxy and alkylthio. In these substituent moieties, each alkyl moiety suitably contains from one to four carbon atoms and is either straight-chain or branched-chain in configuration.

Because of their characteristics, preferred compounds of Formula I are those wherein R is alkyl of from one to twenty carbon atoms; haloalkyl of from one to four carbon atoms substituted by from one to three halogen atoms; alkyl of from one to four carbon atoms substituted by one of alkenyl of from two to four carbon atoms, alkoxy of from one to four carbon atoms, alkoxycarbonyl or alkylcarbonyloxy of from two to four carbon atoms, phenyl or phenoxy substituted by from one to three halogen atoms, trifluoromethyl, alkyl of from one to four carbon atoms or alkoxycarbonyl of from two to four carbon atoms.

In the alkyl moieties, R, it is preferred that the alpha-carbon atom (that bonded to the sulfur atom) have at least one hydrogen atom bonded thereto; it is even more desirable that it have two hydrogen atoms bonded thereto.

The compounds of Formula I may exist as either of two geometric (cis-trans) isomers, depending upon the spatial configuration about the double bond between the carbon atom of the nitromethylene moiety and the ring carbon atom to which it is bonded. The insecticidal activities of the individual isomers may differ. In the cases of the individual species whose preparation is described in the examples, hereinafter, the isomeric content and configuration of the products have not been ascertained. The invention contemplates all of the insecticidally active isomers, and mixtures thereof, both those which result from the method of synthesis, and those which have been deliberately created.

Compounds of Formula I can be prepared by treating a compound of the formula

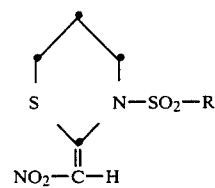
(II)

that is at least partly in solution in an inert solvent, with a suitable halogenating agent. Suitable halogenating agents include bromine, N-chloro- and N-bromo-succinimide, the sulfuryl halides and trifluoromethyl hypofluorite. On the basis of experiments that have been made, chlorine, per se, does not appear to be a suitable chlorinating agent. In the cases of the chlorinating and brominating agents, suitable solvents are haloalkanes, such as methylene chloride, dichloroethane, and the like. In the case of trifluoromethyl hypofluorite, suitable solvents are trichlorofluoromethane, methylene chloride and mixtures thereof. When N-chlorosuccinimide is used, it is advantageous to include azoisobutyronitrile as catalyst. Treatment of the compound of Formula II with N-bromo- or N-chloro-succinimide can be carried out at about room temperature, or somewhat above—e.g., up to about 35° C. Treatment of the compound of Fornula II with bromine or with a sulfuryl halide can be carried out at about 0° C. Treatment of the compound of Formula II with trifluoromethyl hypofluorite is carried out at temperatures of about −30° C. to about 0° C. The products are isolated and purified by conventional procedures and techniques.

Compounds of Formula II can be prepared by treating a compound of the formula

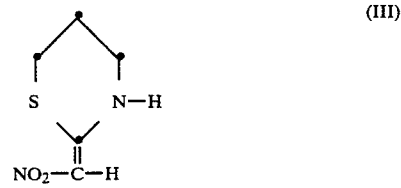
(III)

with the appropriate sulfonyl halide, RSO$_2$Hal wherein Hal is bromine or chlorine, in an inert solvent, in an inert atmosphere, and in the presence of a tertiary amine base as hydrogen halide acceptor. Suitable solvents are haloalkanes, such as methylene chloride, and ethers, such as tetrahydrofuran, or dimethylformamide. The reaction proceeds at satisfactory rates at low temperatures, for example, below 0° C., with temperatures of from about −10° C. to about −75° C. being particularly suitable. Suitable amine bases include trimethylamine, triethylamine and ethyldiisopropylamine. Preferably, the reaction is moderated by employing a solution of the sulfonyl halide in the solvent and adding the solution slowly to the stirred solution of the compound of Formula III and the amine. The products are isolated and purified by conventional procedures and techniques. The preparation and isolation of particular individual species of the compounds of Formula II, in particular instances, is described in application Ser. No. 478600.

Compounds of Formula III and their preparation are described in U.S. Pat. No. 3,993,648. The sulfonyl halides, RSO$_2$Hal, are known compounds, many of them being available commercially.

The preparation, isolation and physical properties of typical individual species of the compounds of Formula I, in particular instances, are described in the following examples. In each case, the identity of the product, and each of any intermediate involved, was confirmed by appropriate chemical and spectral analyses.

EXAMPLE 1

N-(Methylsulfonyl)-2-(bromonitromethylene)-tetrahydro-2H-1,3-thiazine (1)

A solution of 20 g of methanesulfonyl chloride in 150 ml of methylene chloride was added drop-by-drop over a 55 minute period to a stirred mixture of 20 g of 2-(nitromethylene)-tetrahydro-2H-1,3-thiazine and 40 ml of triethylamine in 150 ml of methylene chloride, at −30° C., in a nitrogen atmosphere. The resulting mixture was stirred for 30 minutes at −30° C., and then washed with 2% hydrochloric acid. The aqueous phase was washed twice with methylene chloride. The resulting organic phases were combined, dried (Na$_2$SO$_4$), concentrated to about 50 ml, cooled to 0° C., and filtered. The crystalline solid was triturated with cold methylene chloride, to give N-(methylsulfonyl)-2-(nitromethylene)-tetrahydro-2H-1,3-thiazine (1A), as a crystalline solid, m.p.: 144–145° C. (with decomposition).

9.8 g of recrystallized N-bromosuccinimide was added to a slurry of 11.9 g of (1A) in 300 ml of methylene chloride. The resulting mixture became mildly exothermic (to 32° C.) as the thiazine dissolved. Reaction was complete in about 30 minutes. The reaction mixture was washed with water and stripped of solvent. The residue, an oil, was triturated with water, then dissolved in methylene chloride. The solution was washed with brine, dried (MgSO$_4$), filtered and stripped of solvent. The product was flash-chromatographed over silica gel, using methylene chloride as eluent, to give a solid, which was recrystallized from a 10:1 v:v mixture of isopropyl alcohol and triethylamine, to give (1,) as a yellow solid, m.p. 139°–140° C.

(1) also was prepared as follows:

A solution of 1.6 g of bromine in 10 ml of methylene chloride was added drop-by-drop over a period of 10 minutes to a solution of 2.38 g of (1A) in 50 ml of methylene chloride at 0° C. and under a nitrogen blanket. The resulting mixture was stirred for a further 10 minutes, charcoaled, and stripped of solvent. The residue was dissolved in a minimum amount of methylene chloride, then ether was added to the solution, resulting in a gum. The gum was dissolved in methylene chloride, the solution was charged onto a flash chromatograph column (silica gel) and the product was eluted with methylene chloride, to give (1) on workup.

EXAMPLE 2

N-(Methylsulfonyl)-2-(chloronitromethylene)-tetrahydro-2H-1,3-thiazine (2)

A solution of 1.25 g of redistilled sulfuryl chloride in 5 ml of methylene chloride was added drop-by-drop over a 5-minute period to a slurry of (1A) in 50 ml of methylene chloride in a nitrogen atmosphere at 0–5° C. The mixture was stirred for 30 minutes more, then allowed to warm to room temperature. Two drops more of sulfuryl chloride were added and the mixture was stirred for 5 minutes. The resulting mixture was washed with water, then with brine, dried (MgSO$_4$), and stripped of solvent to give a yellow solid. The solid was triturated with ether to give (2), as a yellow solid, m.p. 149°–151° C. (with decomposition).

(2) also was prepared as follows:

A stirred solution of 0.238 g of (1A), 0.15 g of N-chlorosuccinimide and about 1 mg of azoisobutyronitrile in 10 ml of dichloroethane was refluxed overnight. The resulting mixture was cooled, washed with water, dried (MgSO$_4$) and stripped of solvent, giving a yellow oil. The oil was flash-chromatographed over silica gel, using methylene chloride as eluent, to give (2).

EXAMPLE 3

N-(Dodecylsulfonyl)-2-(bromonitromethylene)-tetrahydro-2H-1,3-thiazine (3)

1.6 g of 2-(nitromethylene)-tetrahydro-2H-1,3-thiazine, 3.18 g of ethyldiisopropylamine and 20 ml of methylene chloride were mixed. The mixture was cooled to and stirred at −60° C. under a nitrogen atmosphere while 2.95 g of dodecanesulfonyl chloride was added in portions over a 10 minute period. The mixture was allowed to warm to 10° C. (2.5 hours), then stirred at 10° C. for 1 hour and at 20° C. for 1.5 hours. The resulting mixture was poured into water, and the organic phase was separated, dried (MgSO$_4$), filtered and stripped of solvent. The residue, a gum, was chromatographed over silica gel, using methylene chloride as eluent. After workup the product was recrystallized from ethanol to give N-(dodecylsulfonyl)-2-(nitromethylene)-tetrahydro-2H-1,3-thiazine (3A) as a solid, m.p.: 116°–117° C.

(3) was prepared, as a yellow solid, m.p.: 70°–71° C., by treating (3A) with N-bromosuccinimide, according to the procedure described in Example 1.

EXAMPLE 4

N-(Dodecylsulfonyl)-2-(chloronitromethylene)-tetrahydro-2H-1,3-thiazine (4)

(4) was prepared, as a yellow solid, m.p.: 76°–77° C., by treating (3A) with N-chlorosuccinimide according to the procedure described in Example 2.

EXAMPLE 5

N-(Phenylmethylsulfonyl)-2-(bromonitromethylene)-tetra-hydro-2H-1,3-thiazine (5)

A solution of 2.29 g of phenylmethanesulfonyl chloride in 20 ml of tetrahydrofuran was added drop-by-drop to a stirred slurry of 1.6 g of 2-(nitromethylene)-tetrahydro-2H-1,3-thiazine and 2.02 g of triethylamine in 10 ml of dry tetrahydrofuran at −50° C. The resulting mixture was stirred at −50° C. for 1 hour, 1.0 g of phenylmethanesulfonyl chloride was added, and the mixture was stirred for a further hour. The mixture was partitioned between methylene chloride and water. The organic phase was separated, washed with water and brine, dried (MgSO$_4$) and stripped of solvent. The residue was flash chromatographed over silica gel, using methylene chloride as eluent, to give N-(phenylmethylsulfonyl)-2-(nitromethylene)-tetrahydro-2H-1,3-thiazine (5A), as a pale yellow solid, m.p.: 140°–141° C.

(5) was prepared, as a yellow solid, m.p.: 143° C. (with decomposition), by treating (5A) with N-bromosuccinimide according to the procedure described in Example 1.

EXAMPLE 6

N-(Phenylmethylsulfonyl)-2-(chloronitromethylene)-tetrahydro-2H-1,3-thiazine (6)

(6) was prepared, as a yellow solid, m.p.: 150°–151° C. (with decomposition), by treating (5A) with N-chlorosuccinimide according to the procedure described in Example 2.

Another individual species of the compounds of Formula I is N-(methylsulfonyl)-2-(fluoronitromethylene)-tetrahydro-2H-1,3-thiazine, formed by treating Compound (1A) (Example 1) in solution in trifluorochloromethane, methylene chloride or a mixture of those two, at a temperature of from about −30° C. to about 0° C.

Compounds of Formula I have been found to possess useful insecticidal activity, and to be comparatively stable to light and oxidation. Compounds of Formula I are of particular interest for control of the larval (caterpillar or "worm") forms of insects of the genus Heliothis, such as *H. zea* (corn earworm, cotton bollworm, tomato fruitworm), the genus Spodoptera, such as *S. littoralis* (Egyptian cotton leafworm).

Accordingly, this invention includes a method for controlling insect pests at a locus which comprises applying to the locus an effective amount of at least one compound of Formula I. For such use, the active compound is ordinarily most effectively applied when formulated with a carrier, or a surface-active agent, or both. Therefore, this invention also includes pesticidal compositions which comprise a carrier, or a surfactant or both, together with a pesticidally effective amount of at least one compound of Formula I.

The term "carrier" as used herein means an inert, horticulturally acceptable material (i.e., non-phytotoxic when applied to plants), that may be inorganic or organic and of synthetic or natural origin with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride annd styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example superphosphates.

Suitable liquid carriers include solvents for the compound of this invention and liquids in which the toxicant is insoluble or only slightly soluble.

Examples of such solvents and liquid carriers, generally, are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils, chlorinated hydrocarbons, such as methylene chloride, perchlorethylene, trichloroethane, including liquified, normally vaporous, gaseous compounds. Mixtures of different liquids are often suitable.

If used, the surface-active agent may be an emulsifying agent or a dispersing agent or a wetting agent. It may be nonionic, ionic or preferably, mixtures of both. Surface-active agents usually applied in formulating pesticides may be used. Examples of such surface-active agents are the sodium or calium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols; encapsulated formulations and controlled release formulations are also contemplated, as are bait formulations. Wettable powders are usually compounded to contain 25, 50 or 75% w of toxicant and usually contain, in addition to solid carrier, 3–10% w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing 0.5–10% w of toxicant. Granules may be manufactured by extrusion of plastics, agglomeration or impregnation techniques. Generally, granules will contain 0.5–25% w toxicant and 0–10% w of additives such as stabilizers, slow release modifiers and binding agents. Emulsifiable concentrates usually contain, in addition to the solvent, and when necessary, cosolvent, 10–50% w/v toxicant, 2–20% w/v emulsifiers and 0–20% w/v of appropriate additives such as stabilizers, penetrants and corrosion inhibitors. Suspension concentrates are compounded so as to obtain a stable, nonsedimenting, flowable product and usually contain 10–75% w toxicant, 0–5% w of dispersing agents, 0.1–10% w of suspending agents such as protective colloids and thixotropic agents, 0–10% w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention can also contain other ingredients, for example, other compounds possessing pesticidal, herbicidal or fungicidal properties, or attractants, such as pheromones, attractive food ingredients, and the like, for use in baits and trap formulations.

The compositions of the invention are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect or acarine species to be controlled and the like, proper consideration and resolution of these factors to provide the necessary dosage of active material at the locus being within the skill of those versed in the art. In general, however, the effective dosage of toxicants of this invention at the locus to be protected—i.e. the applied dosage—is of the order of 0.01% to 0.5% based on the total weight of the formulation, though under some circumstances the effective concentration will be as little as 0.001% or as much as 2%, on the same basis.

Activity of individual species of Formula I with respect to insect pests was determined by using standardized test methods to ascertain the toxicity of the compounds as follows:

I. Corn earworm larvae (*Heliothis zea* (Boddie) were tested by spraying a broad bean plant with dilutions of acetone solution of test compound into water containing an emulsifier. Immediately after spraying, 5 larvae were transferred to the plant and held for 44–46 hours, at which time the dead and moribund larvae were counted. The tests were conducted employing several different dosage rates for each test compound.

In each instance, the toxicity of the compound of the invention was compared to that of a standard pesticide (Parathion), its relative toxicity then being expressed in terms of the relationship between the amount of compound of the invention and the amount of the standard pesticide required to produce the same percentage (50) of mortality in the test insect. By assigning the standard pesticide an arbitrary rating of 100, the toxicities of the compounds of the invention were expressed in terms of the toxicity indices, which compares the toxicity of the compounds of the invention with that of the standard pesticide. That is to say, a test compound having a Toxicity Index of 50 would be half as active, while one having a Toxicity Index of 200 would be twice as active as the standard pesticide. The Toxicity Indices are set forth in Table 1.

TABLE 1

| Compound No. | Toxicity Index |
|---|---|
| 1 | 2100 |
| 2 | 220 |
| 3 | 310 |
| 4 | 200 |
| 5 | 1100 |
| 6 | 250 |

II. The insecticidal activities of individual species of Formula I also were assessed with respect to *Spodoptera littoralis*, as follows:

In each test a 0.2% solution or suspension of each test compound in 16.7% acetone in water containing 0.04% Triton X-100 (as surfactant) was used, as was a control solution of water, acetone and Triton X-100 in the same proportions. The tests were all conducted under normal insectary conditions 23° C.±2° C. (fluctuating light and humidity). Each test solution and the control solution was sprayed onto a separate petri dish containing a diet on which the *S. littoralis* larvae had been reared. When the spray deposit had dried each dish was infested with ten second instar larvae. Mortality assessments were made 1 and 7 days after spraying and the percentage mortality calculated.

The results of these tests are shown in Table 2.

TABLE 2

| | PESTICIDAL ACTIVITY | |
|---|---|---|
| | *Spodoptera littoralis* | |
| Compound | 24 Hr | 7 Day |
| 1 | A[a] | A |
| 2 | A | A |

[a]A denotes 90–100% mortality; B denotes 50–80% mortality; C denotes 0–40% mortality.

Compounds of Formula I have been tested with respect to their persistence after they were applied to a surface and exposed to light, and have been compared in this respect to, and found to be significantly more persistent than, corresponding N-unsubstituted compounds of U.S. Pat. No. 3,993,648. Compounds of Formula I were found to be more stable to light than were those of the patent.

We claim:

1. A compound of the formula

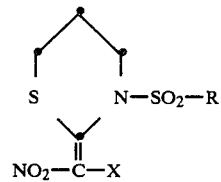

wherein X is bromine, chlorine or fluorine and R contains up to 20 carbon atoms and is alkyl or alkyl substituted by one or more halogen atoms, or alkoxy, alkylcarbonyl, alkylcarbonyloxy, alkyloxycarbonyl, alkenyl, or phenyl or phenoxy which may be substituted by one or more of halogen, haloalkyl, cyano, nitro, and alkyl, alkoxy or alkoxythio of from one to four carbon atoms.

2. A compound according to claim 1 wherein R is alkyl of from one to 20 carbon atoms, haloalkyl of from one to four carbon atoms substituted by from one to three halogen atoms, or is alkyl of from one to four carbon atoms substituted by one of alkenyl of from two to four carbon atoms, alkoxy of from one to four carbon atoms, alkoxycarbonylalkyl or alkylcarbonyloxy of from two to four carbon atoms, phenyl or phenoxy substituted by from one to three halogen atoms, trifluoromethyl, alkyl of from one to four carbon atoms or alkoxycarbonyl of from two to four carbon atoms.

3. A compound according to claim 2 wherein the alkyl moiety R has a hydrogen atom bonded to the alpha-carbon atom.

4. A compound according to claim 2 wherein the alpha-carbon atom is bonded to two hydrogen atoms.

5. A method for controlling insects at a locus which comprises applying to said locus an effective amount of a compound of claim 1.

6. A method for controlling insects at a locus which comprises applying to said locus an effective amount of a compound of claim 2.

7. A insecticidal composition comprising an effective amount of a compound of claim 1 together with a horticulturally acceptable carrier, and optionally a surface-active agent.

8. A insecticidal composition comprising an effective amount of a compound of claim 2 together with a horticulturally acceptable carrier, and optionally a surface-active agent.

* * * * *